United States Patent [19]
Kourtakis et al.

[11] Patent Number: 5,543,532
[45] Date of Patent: Aug. 6, 1996

[54] CATALYST AND METHOD FOR VAPOR PHASE OXIDATION OF ALKANE HYDROCARBONS

[75] Inventors: Kostantinos Kourtakis, Hockessin; George C. Sonnichsen, Wilmington, both of Del.

[73] Assignee: E. I. Du Pont de Nemours and Company, Wilmington, Del.

[21] Appl. No.: 221,292

[22] Filed: Mar. 31, 1994

[51] Int. Cl.$^6$ .................... C07D 307/34; B01J 27/198
[52] U.S. Cl. ............................ 549/260; 502/209
[58] Field of Search ............... 549/260; 502/209

[56] References Cited

U.S. PATENT DOCUMENTS

| | | | |
|---|---|---|---|
| 3,864,280 | 2/1975 | Schneider | 252/435 |
| 3,985,775 | 10/1976 | Harrison | 260/346.8 A |
| 4,043,943 | 8/1977 | Schneider | 252/437 |
| 4,062,873 | 12/1977 | Harrison | 260/346.75 |
| 4,064,070 | 12/1977 | Harrison | 252/435 |
| 4,111,963 | 9/1978 | Mount et al. | 260/346.75 |
| 4,132,670 | 1/1979 | Katsumoto et al. | 252/437 |
| 4,147,661 | 4/1979 | Higgins et al. | 252/435 |
| 4,178,304 | 12/1979 | Litvishkov et al. | 260/465 E |
| 4,187,235 | 2/1980 | Katsumoto et al. | 260/346.75 |
| 4,219,484 | 8/1980 | Milberger et al. | 260/346.75 |
| 4,337,173 | 6/1982 | Otake | 252/435 |
| 4,371,702 | 2/1983 | Bither, Jr. | 549/260 |
| 4,442,226 | 4/1984 | Bither, Jr. | 502/209 |
| 4,567,314 | 1/1986 | Robinson et al. | 585/621 |
| 4,647,673 | 3/1987 | Bremer et al. | 549/260 |
| 4,668,802 | 5/1987 | Contractor | 549/259 |
| 4,769,477 | 9/1988 | Bergna | 549/259 |
| 5,021,588 | 6/1991 | Contractor | 549/259 |
| 5,364,824 | 11/1994 | Andrews et al. | 549/260 |

FOREIGN PATENT DOCUMENTS 0518548 12/1992 European Pat. Off. ........ C07C 53/08

OTHER PUBLICATIONS

Hutchings, G., *Applied Catalysis*, 72, 1–32, 1991.
Zazhigalov, V. et al., *Kinetika i Kataliz*, 31:5, 1219–1223, Sep.–Oct. 1990.
Matsuura, I, *Hyomen*, 20, No. 11, 605–631, 1982.
Shima, K. et al., *Res. Dev. Rev.*, 4, No. 1, 18–24, 1990.

*Primary Examiner*—Bernard Dentz

[57] ABSTRACT

This invention relates to cation substituted catalysts based primarily upon vanadium pyrophosphate, useful in the oxidation of alkane hydrocarbons.

7 Claims, 4 Drawing Sheets

FIG.1

CATALYST AND METHOD FOR VAPOR PHASE OXIDATION OF ALKANE HYDROCARBONS

FIELD OF THE INVENTION

This invention relates to cation substituted catalysts, preferably in the form of solid solutions, based primarily upon vanadium pyrophosphate, useful as catalysts for the oxidation of alkane hydrocarbons, particularly the production of maleic anhydride by the vapor phase oxidation of n-butane.

BACKGROUND OF THE INVENTION

Maleic anhydride is used as a raw material for products ranging from agricultural chemicals, paints, paper sizing and food additives to synthetic resins. To fill the high demand for this valuable chemical, a variety of commercial processes have been developed, the most successful of which involves the vapor phase oxidation of n-butane to maleic anhydride in the presence of a vanadium-phosphorus-oxygen (VPO) catalyst. Since the development of this method in the 1970's, research has continued to continuously improve the reaction conditions and, particularly, the VPO catalysts.

A review of the improvements made in this technology is given by G. J. Hutchings, in Applied Catalysis, Elsevier Science Publishers B. V. Amsterdam, 72(1991), pages 1–31. The preferred method of preparation of VPO catalysts is the hydrochloric acid digestion of $V_2O_5$ and $H_3PO_4$ in either an aqueous solvent or non aqueous solvent, such as methanol, tetrahydrofuran (THF) or isobutanol, followed by solvent removal to give what is termed the catalyst precursor, which is then activated by heating. Vanadium, phosphorus and oxygen can form a large number of distinct compounds which have been well characterized, e.g., $\alpha$-$VOPO_4$, $\gamma$-$VOPO_4$, $VOHPO_4$, $(VO)_2P_2O_7$, $VO(PO_3)_2$ and $VO(H_2PO_4)_2$, the most active catalytic phase believed to be $(VO)_2P_2O_7$. While the predominant oxide phase in VPO catalysis is $(VO)_2P_2O_7$, the VPO catalysts are usually referred to as "mixed oxides" in recognition of the probable presence of other oxide phases. VPO catalysts have V:P atomic ratios typically in the range of 1:1–1.2 and average, bulk vanadium oxidation states in the range 4.0–4.3. One of the major methods employed to improve the performance of VPO catalysts involved the use of promoters.

In general the methods of preparing promoted catalysts are the same as those described for the unpromoted catalysts. Promoter compounds can be added either (a) together with the vanadium and phosphorus compounds prior to the preparation of the catalyst precursor, or (b) by impregnation of the catalyst precursor prior to formation of the final catalyst by heat treatment. Vanadium/phosphorus/silicon catalyst compositions made in an organic medium are known. Also known are processes for preparing high surface area VPO catalysts. Such catalysts containing up to 0.2 mole, per mole of vanadium, of a transition, alkali or alkaline earth metal, for example, tantalum, titanium, niobium, antimony, bismuth or chromium have also been disclosed. An improved VPO catalyst containing the promoter comprising silicon and at least one of indium, antimony, and tantalum has also been taught.

A number of cations, e.g., Co, Fe, Li, Zn, Ce, Mn, Sn and Lu, are believed to form solid solutions in $(VO)_2P_2O_7$. U.S. Pat. No. 4,337,173 discloses a promoted VPO catalyst comprising a substitutional solid-solution type crystalline oxide represented by the general formula $[(V_{1-x-y-z}Fe_xCr_yAl_z)O]_2P_2O_7$, wherein $0 \leq x \leq 0.40$, $0 \leq y \leq 0.40$, $0 \leq z \leq 0.40$, and $x+y+z \leq 0.40$, which has the same crystal structure as $(VO)_2P_2O_7$. Promoters which these authors propose could be in solid solution with the $(VO)_2P_2O_7$ phase appear to be effective in very low concentrations.

In spite of the progress in catalyst and process development over the years, a need still remains to continue to improve the VPO catalyst and it is to that end that this invention is directed.

SUMMARY OF THE INVENTION

The invention provides for an improved VPO catalyst for the oxidation of alkane hydrocarbons comprising a crystalline oxide of formula I through IV:

$$(V_{1-x-y}A_xB_yO)_2P_2O_7 \pm \delta \qquad\qquad\qquad I$$

$$(V_{1-x}A_xO)_2P_{2-y}B_yO_7 \pm \delta \qquad\qquad\qquad II$$

$$(V_{1-y}B_yO)_2P_{2-x}A_xO_7 \pm \delta \qquad\qquad\qquad III$$

$$(VO)_2P_{2-x-y}A_xB_yO_7 \pm \delta \qquad\qquad\qquad IV$$

wherein A is at least one of the cations selected from the group consisting of Sb, As, and Bi; B is at least one of the cations selected from the group consisting of Ge, Sb, Pb, Al, Ga, Tl, Sc, V, Cr, Mn, Fe, Co, Ni, Cu, Zn, Y, Zr, Nb, Mo, Ru, Rh, Pd, Ag, Cd, La, Hf, W, Re, Os, Ir, Pt, Au, Ho, Be, Mg, Ca, Sr, Ba, Ra, Li, Na, K, Rb, Cs, and the rare earths, including Ce, Pr, Nd, Sm, Eu, Gd, Tb, Dy, Ho, Er, Tm, Yb, Lu, Th, Pa, U; $\delta$ is 0 to less than 0.5, and x and y are as follows:

in formula I: $0.7 \geq x > 0$ for each A, $0.7 \geq y > 0$ for each B, and $0.7 \geq (x+y) > 0$;

in formula II: $0.7 \geq x > 0$ for each A, and $1.0 \geq y > 0$ for each B;

in formula III: $1.0 \geq x > 0$ for each A, and $0.7 \geq y > 0$ for each B; and in formula IV: $1.0 \geq x > 0$ for each A, $1.0 \geq y > 0$ for each B, and $1 \geq (x+y) > 0$.

The catalyst in accordance with this invention is believed to provide increased oxygen capacity in the catalyst's crystal lattice, i.e., the mobile or "reactive" oxygen contained in the catalyst. In the case of the oxidation of n-butane, the catalyst in accordance with this invention is believed to be selective to maleic anhydride and/or to provide increased selectivity towards maleic anhydride by the oxidation of n-butane in the absence of gas phase oxygen. Increases in selectivity towards maleic anhydride by, for instance, an increase in the selective "reactive" oxygen in the crystalline lattice ultimately leads to overall improvements in the yields of maleic anhydride from the n-butane oxidation process.

DETAILED DESCRIPTION OF THE INVENTION

The improved VPO catalyst of present invention as described above as formula I through IV is made by a process similar to that described in U.S. Pat. No. 4,442,226, herein incorporated by reference, wherein the vanadium is in the +5 oxidation state, such as in $V_2O_5$ or $NH_4VO_3$, and is initially reduced to a substantial degree to the +4 oxidation state by reaction in either an aqueous or organic liquid medium. The reductant can comprise a soluble inorganic compound, such as a halide acid, for example, concentrated hydrochloric acid; a reduced acid of phosphorus, for example, $H_3PO_3$; or a soluble organic compound, for example, formaldehyde, ethylene glycol, or glycolic, oxalic, citric or tartaric acid. In an organic medium, the preferred medium herein, the reductant can comprise one or more alcohols selected from such species as n-propyl, isopropyl, n-butyl, isobutyl, and benzyl alcohols. The reduction can be brought about by slurrying the pentavalent vanadium compound in the liquid medium, followed by heating under reflux for the time necessary to bring about the reduction.

The improvement in the VPO catalyst of this invention, which leads to enhanced productivity of maleic anhydride, results from the introduction of promoter AB into the $(VO)_2P_2O_7$ crystal structure, preferably introduced in a specific order and chemical form, i.e., solid solution, following the reduction step in which the tetravalent vanadium is formed. As indicated, the promoter cation moieties comprise at least one of As, Sb and Bi with at least one of Ge, Sb, Pb, Al, Ga, Tl, Sc, V, Cr, Mn, Fe, Co, Ni, Cu, Zn, Y, Zr, Nb, Mo, Ru, Rh, Pd, Ag, Cd, La, Hf, W, Re, Os, Ir, Pt, Au, Ho, Be, Mg, Ca, Sr, Ba, Ra, Li, Na, K, Rb, Cs, and the rare earths, including Ce, Pr, Nd, Sm, Eu, Gd, Tb, Dy, Ho, Er, Tm, Yb, Lu, Th, Pa, U. The most preferred combination is Sb and Fe.

The formulae used herein above to describe the catalysts of this invention are intended to clarify that the specific placement of the cation substituents in the crystal lattice can vary. For example, the cations can be placed in whole or in part on a vanadium site in the crystal lattice, or the cations can be placed in whole or in part on a phosphorus site. In any event, this method of introduction of cation substituent into the crystal lattice is distinguished from those in the art where one or more cation substituents are post-deposited on the surface of the VPO composition. X-ray diffraction data, detailed below in the Examples, show that many of the catalysts in accordance with this invention crystallize as a vanadium pyrophosphate or pyrophosphate-like structure.

Although not essential to the basic performance of the improved catalyst of this invention, it is preferred that the cation substituents be introduced into the reaction medium as the inorganic salts, and not the metal oxides. Thus, in the organic system, they can be added as a cation with an appropriate attendant anion, for example, an acetate, alkoxide, anhydrous halide or acetylacetonate.

Following substantial reduction of the +5 vanadium to the tetravalent species and the introduction of the requisite promoters or promoter precursors, the catalyst precursor is formed by the addition of any commonly used appropriate phosphorus compound, for example, anhydrous phosphoric acid with the continued heating of the resultant mixture under reflux to give the catalyst precursor composition that can be isolated by filtration, following cooling of the slurry to room temperature. This product is subsequently dried at about 125° C. to about 200° C. in a flowing inert atmosphere, such as nitrogen, for approximately 12 hours. At this point, oftentimes it is a crystalline species having an x-ray diffraction pattern similar to that of $VO(HPO_4)$ ½$H_2O$, the precursor to vanadium phosphate catalyst.

This catalyst precursor is then calcined and activated in a fluidized reactor to generate the active catalyst phase. A typical activation procedure is detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air, and

360° C.–25° C. in $N_2$.

This catalyst precursor is then formed into a convenient catalyst shape, for ultimate charge into a reactor, by pelletizing the catalyst typically at about 30,000 psi ($2.07 \times 10^8$ Pa) or less, to form small disks and crushing the pellet through sieves. For fixed bed reactor evaluations, typically a −40, +60 mesh is used (U.S. Sieve Series). Optionally, one could blend the resultant powder with 1–3% of a die lubricant and pellet binder, such as graphite or Sterotex®, a hydrogenated cottonseed oil, commercially available from Capital City Products Company, Columbus, Ohio, before tabletting.

For fluidized bed reactor use, however, catalysts prepared in the above manner may not have the optimum particle size range for such a reactor. Hence, they must be formed in the correct particle size range. Attrition by abrasion and/or fracture of the particles is a frequent problem in fluidized reactors, which necessitates the addition of a binder to the catalyst particles. Excessive particle attrition in these reactors is caused, for example, by particle-to-particle contact, abrasion with bed walls and bed internals, as well as distributor jet impingement and abrasion in circulation conduits leading to and from the reactor bed. High particle attrition contributes to product contamination and catalyst loss, plugging of down stream equipment, high filtration costs, and unstable fluidization behavior such as channeling, slugging or increased entrainment of reactants. The deleterious effects of fluidized bed operations can be exacerbated by high temperature conditions. These catalysts, by themselves, cannot be formed in the correct particle size range with sufficient mechanical strength to be attrition resistant.

In addition to mechanical strength, particle shape can also have an impact on attrition. Spheroidal particles with smooth surfaces will have lower attrition losses than particles with irregular shapes and rough edges. Spheroidal is defined herein to include spherical and nearly spherical particles, so long as there are no irregular or sharp edges that would likely cause attrition during handling or fluidization.

Conventionally, an abrasion resistant coating of silica is used to make these spheroidal particles (or microspheres) attrition resistant. U.S. Pat. No. 4,769,477 teaches such an abrasion resistant coating which is contemplated for potential use within the confines of this invention without departing from the spirit thereof. Commonly a silica coating is applied by (a) forming a slurry comprised of catalyst or catalyst precursor particles dispersed in an aqueous silicic acid solution equivalent to a weight of $SiO_2$ not exceeding about 6% by weight, the relative amounts of the particles and silicic acid chosen so that the weight of the $SiO_2$ formed is about 3–15% of the total weight of the particles and the $SiO_2$, (b) spray drying the slurry to form porous microspheres of attrition resistant catalyst or catalyst precursor and (c) calcining the spray dried microspheres at an elevated temperature which is below the temperature which is substantially deleterious to the catalyst, to produce attrition resistant $SiO_2$ coated catalyst. Preferably, the silicic acid is polysilicic acid having an equivalent concentration of $SiO_2$ not exceeding about 5% by weight; the catalyst or catalyst precursor particles are less than about 10 µm in diameter; the microporous spheroidal particles produced by spray drying have diameters of from about 10 µm to about 300 µm, and the relative amounts of particles to be spray dried and $SiO_2$ are chosen so that the weight of the $SiO_2$ is about 5–12% of the total weight of the particles and the $SiO_2$. It is preferred that the size of the particles used in step (a) above are from about 0.5 µm to about 10 µm and most preferably from about 0.5 µm to about 3 µm.

The catalyst of the invention can be utilized advantageously with regard to conversion and selectivity in the wide variety of conventional techniques and reactor configurations employed to conduct the vapor phase oxidation of alkane hydrocarbons, particularly n-butane to maleic anhydride. For example, the conversion can be conducted in a fixed-bed reactor, whereby the catalyst particles are maintained in a fixed position and are contacted with alkane hydrocarbon and oxygen in appropriate amounts, in the presence of one or more inert diluent gases. The greatest advantages of using the catalyst of this invention are realized when the conversion of n-butane to maleic anhydride is carried out in a recirculating solids reactor, such as that described in U.S. Pat. No. 4,668,802. This patent discloses an improved process for the selective vapor phase oxidation of n-butane to maleic anhydride over a VPO catalyst, whereby the amount of oxygen in the feed gas to the VPO catalyst is limited to less than the stoichiometric amount required for the total amount of n-butane converted in the process. The reduced catalyst resulting from the oxidation is separated from the gaseous product stream; and is reoxidized, optionally in a separate reaction zone, before being contacted with n-butane.

While the present invention is not bound by theory of, it is believed that the increased oxygen capacity of the catalyst of this invention, selective to maleic anhydride, allows this catalyst to effectively catalyze high conversion to maleic anhydride, even under conditions where the catalyst is completely reduced or is the only source of oxygen for n-butane. This behavior is contrasted with prior art catalysts and promoted catalysts, such as that described in U.S. Pat. No. 4,442,226, wherein the VPO or promoted VPO catalysts are sensitive to the partial pressure of oxygen with respect to their catalytic activity and it is recommended that the partial pressure of oxygen in the feed be maximized within the limits of safe operability. Use of the catalyst of the present invention, consequently, provides advantages in safety of operation as well as conversion, because one can operate at levels of oxygen in the feed which are well outside the explosive range of conventionally required butane/oxygen/inert gas mixtures.

Catalysts used in most oxidation systems can comprise particles in the approximate size range 100–325 mesh (U.S. Sieve Series). The desired particle size distribution for the catalyst of the present invention may also be achieved by spray drying slurries of the catalyst precursor at appropriate concentrations. To enhance attrition resistance, variable amounts of support, such as silica, can be incorporated into the fluid-bed catalyst system by addition of colloidal silica sol, for example, as one of the Ludox® colloidal silica compositions commercially available from E. I. du Pont de Nemours and Company, Wilmington, Del., or a very fine silica powder, such as one of the Cab-O-Sil® fumed silica commercially available from Cabot Corporation, Tuscoloa, Ill.

EXAMPLES

The formula listed for each of Examples A, 1, 4, 11, 20, 21, 25, and 26 are exact due to the X-ray crystallographic date presented. For the remainder of the examples, formula I is used. However, these Examples could also be represented by formula II, III, or IV since structure studies have not been completed.

EXAMPLE 1

Preparation of $(V_{0.9}Sb_{0.05}Fe_{0.05}O)_2P_2O_7$

A 3 liter round bottom flask was equipped with an addition funnel, mechanical stirrer and a reflux condenser. For the duration of the reflux, nitrogen gas was used to purge the apparatus. In an inert atmosphere drybox containing nitrogen gas, 81.85 g of air micronized vanadium pentoxide (Aldrich Chemicals, Milwaukee, Wis.) was added to the round bottom flask. 8.11 g of anhydrous iron (III) chloride (Johnson, Matthey—Alfa Chemicals, Ward Hill, Mass.) and 17.06 g of antimony (III) butoxide (JM, Alfa Chemicals) were then added. To this mixture, 1034 ml of isobutyl alcohol (anhydrous, Aldrich Chemicals) and 95 ml of benzyl alcohol (anhydrous, Aldrich Chemicals) were added. The round bottom flask was then stoppered and brought outside of the drybox. Anhydrous phosphoric acid was prepared in the inert atmosphere dry box by mixing 85.8 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids were then filtered in a buchner funnel and dried in flowing nitrogen at 80°–125° C. for a period of 16 hours to yield the catalyst precursor.

Following this procedure, the precursor was directly calcined and activated in a small, 4 cm fluidized bed reactor. Prior to the activation, fine particles were sieved out by using a 400 mesh screen. The calcination/activation procedure generated the active catalyst phase by subjecting the precursor to the thermal conditions detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

The resulting catalyst was analyzed by Scanning Transmission Electron Microscopy (STEM) and High Resolution Transmission Electron MicrosCopy (HREM) using a commercially available Philips CM30 Super Twin HREM/STEM system operated at 300 keV for atomic scale imaging and high spatial resolution chemical composition analysis with the energy dispersive X-ray analyzer (EDX) and a STEM probe size of about 5 nanometers. The catalyst sample was supported on a carbon-filmed microscope grid. Chemical analyses spectra were obtained from a large number of crystals and from a number of regions within each crystal. The data showed that Fe and Sb cations were homogeneously distributed. The corresponding HREM lattice images showed regular periodicity with lattice lines extending directly to the surface with no evidence of an amorphous surface phase, line dislocations or stacking defects. The HREM/STEM data supported the formation of a solid solution in this catalyst.

EXAMPLE 2

Preparation of $(V_{0.98}Sb_{0.01}Fe_{0.01}O)_2P_2O_7\pm\delta$

A 3 liter round bottom flask was equipped with an addition funnel, mechanical stirrer and a reflux condenser. For the duration of the reflux, nitrogen gas was used to purge the apparatus. In an inert atmosphere drybox containing nitrogen gas, 89.12 g of air micronized vanadium pentoxide (Aldrich Chemicals, Milwaukee, Wis.) was added to the round bottom flask. 1.62 g of anhydrous iron (III) chloride (Johnson, Matthey—Alfa Chemicals, Ward Hill, Mass.) and 3.41 g of antimony (III) butoxide (JM, Alfa Chemicals) were then added. To this mixture, 1000 ml of isobutyl alcohol (anhydrous, Aldrich Chemicals) and 95 ml of benzyl alcohol (anhydrous, Aldrich Chemicals) were added. The round bottom flask was then stoppered and brought outside of the drybox. Anhydrous phosphoric acid was prepared in the inert atmosphere drybox by mixing 85.8 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids are then filtered in a buchner funnel and dried in flowing nitrogen at 125° C. for a period of 16 hours.

Following this procedure, the precursor was directly calcined and activated in a small, 4 cm fluidized bed reactor, to generate the active catalyst phase by subjecting the precursor to the thermal conditions detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

Prior to the activation, fine particles were sieved out by using a 400 mesh screen.

EXAMPLES 3–5

Preparation of $(V_{1-x-y}Sb_xFe_yO)_2P_2O_7\pm\delta$

The procedure described in Example 2 was used to prepare additional catalysts. The cation sources shown in Table I were employed in the molar ratios shown. The formula of the catalysts produced were $(V_{0.8}Sb_{0.1}Fe_{0.1}O)_2P_2O_7\pm\delta$, $(V_{0.9}Sb_{0.025}Fe_{0.075}O)_2P_2O_7$, and $(V_{0.9}Sb_{0.075}Fe_{0.025}O)_2P_2O_7\pm\delta$.

EXAMPLE 6

Preparation of $(V_{0.9}Sb_{0.05}Fe_{0.05}O)_2P_2O_7\pm\delta$

A procedure similar to that of Example 1 was used. A 3 liter round bottom flask was equipped with an addition funnel, mechanical stirrer and a reflux condenser. For the duration of the reflux, nitrogen gas was used to purge the apparatus. Vanadium pentoxide was air micronized to prior to use. In an inert atmosphere drybox containing nitrogen gas, 89.89 g of vanadium pentoxide (Aldrich Chemicals, Milwaukee, Wis.) was added to the round bottom flask. 8.91 g of anhydrous iron (III) chloride (Johnson, Matthey—Alfa Chemicals, Ward Hill, Mass.) and 16.45 g of antimony pentachloride (anhydrous) (JM, Alfa Chemicals) were then added. To this mixture, 1034 ml of isobutyl alcohol (anhydrous, Aldrich Chemicals) and 95 ml of benzyl alcohol (anhydrous, Aldrich Chemicals) were added. The round bottom flask was then stoppered and brought outside of the drybox. Anhydrous phosphoric acid was prepared in the inert atmosphere drybox by mixing 88.79 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids were then filtered in a buchner funnel and dried in flowing nitrogen at 125° C. for a period of 16 hours to yield the catalyst precursor.

Following this procedure, the precursor was directly calcined and activated in a small, 4 cm fluidized bed reactor, to generate the active catalyst phase by subjecting the precursor to the thermal conditions detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

Prior to the activation, fine particles were sieved out by using a 400 mesh screen.

EXAMPLE 7

Preparation of $(V_{0.9}Sb_{0.05}Fe_{0.05}O)_2P_2O_7\pm\delta$

A procedure similar to that of Example 1 was used. A 3 liter round bottom flask was equipped with an addition funnel, mechanical stirrer and a reflux condenser. For the duration of the reflux, nitrogen gas was used to purge the apparatus. Vanadium pentoxide was air micronized to prior to use. In an inert atmosphere drybox containing nitrogen gas, 89.89 g of vanadium pentoxide (Aldrich Chemicals, Milwaukee, Wis.) was added to the round bottom flask. 8.91 g of anhydrous iron (III) chloride (Johnson, Matthey—Alfa Chemicals, Ward Hill, Mass.) and 18.73 g of antimony butoxide (JM, Alfa Chemicals) were then added. To this mixture, 1034 ml of isobutyl alcohol (anhydrous, Aldrich Chemicals) and 95 ml of benzyl alcohol (anhydrous, Aldrich Chemicals) were added. The round bottom flask was then stoppered and brought outside of the drybox. Anhydrous phosphoric acid was prepared in the inert atmosphere drybox by mixing 85.79 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brought outside of the drybox, and attached to the round bottom flask. The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids were then filtered in a buchner funnel and dried in flowing nitrogen at 125° C. for a period of 16 hours to yield the precursor catalyst.

Following this procedure, the precursor was directly calcined and activated in a small, 4 cm fluidized bed reactor, to generate the active catalyst phase by subjecting the precursor to the thermal conditions detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

Prior to the activation, fine particles were sieved out by using a 400 mesh screen.

EXAMPLES 8–13

Preparation of $(V_{1-x-y}A_xB_yO)_2P_2O_7\pm\delta$

The procedure described in Example 7 was used to prepare additional catalysts. The cation sources were as shown in Table I and were used in the molar ratios shown. The formula of the catalysts produced were $(V_{0.9}Sb_{0.05}Fe_{0.05}O)_2P_2O_7\pm\delta$, $(V_{0.8}Sb_{0.1}Fe_{0.10})_2P_2O_7\pm\delta$, $(V_{0.8}Sb_{0.15}Fe_{0.05}O)_2P_2O_7\pm\delta$, $(V_{0.9}Sb_{0.05}Cu_{0.05}O)_2P_2O_7$, $(V_{0.9}Sb_{0.05}Cu_{0.05}O)_2P_2O_7\pm\delta$, and $(V_{0.9}Sb_{0.05}Mn_{0.05}O)_2P_2O_7\pm\delta$.

EXAMPLE 14

Preparation of $(V_{0.8}Sb_{0.1}Mn_{0.1}O)_2P_2O_7$

An 8 liter round bottom flask was equipped with an addition funnel, mechanical stirrer and a reflux condenser. For the duration of the reflux, nitrogen gas was used to purge the apparatus. In an inert atmosphere drybox containing nitrogen gas, 239.7 g of vanadium pentoxide (Aldrich Chemicals, Milwaukee, Wis.) was added to the round bottom flask. The vanadium pentoxide was then air micronized. 83.41 g of manganese (II) acetyl acetonate (Johnson, Matthey—Alfa Chemicals, Ward Hill, Mass.) and 112.38 g of antimony (III) butoxide (JM, Alfa Chemicals) were then added. To this mixture, 3102 ml of isobutyl alcohol (anhydrous, Aldrich Chemicals) and 285 ml of benzyl alcohol (anhydrous, Aldrich Chemicals) were added. The round bottom flask was then stoppered and brought outside of the drybox. Anhydrous phosphoric acid was prepared in the inert atmosphere dry box by mixing 257.37 g of 85+% phosphoric acid (J. T. Baker and Co., Phillipsburg, N.J.) with 99.6 g of phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids are then filtered in a buchner funnel and dried in flowing nitrogen at 125° C. for a period of 16 hours to yield the catalyst precursor.

Following this procedure, the precursor was directly calcined and activated in a small, 4 cm fluidized bed reactor, to generate the active catalyst phase by subjecting the precursor to the thermal conditions detailed below:

25°–390° C. in air

390° C. 1 hour in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

Prior to the activation, fine particles were sieved out by using a 400 mesh screen.

EXAMPLES 15–17

Preparation of $(V_{1-x-y}A_xB_yO)_2P_2O_7\pm\delta$

The procedure described in Example 7 was used to prepare additional catalysts. The cation sources were as shown in Table I and were used in the molar ratios shown. The formula of the catalysts produced were $(V_{0.9}Sb_{0.05}Al_{0.05}O)_2P_2O_7\pm\delta$, $(V_{0.6}Sb_{0.2}Al_{0.2}O)_2P_2O_7\pm\delta$, and $(V_{0.8}Sb_{0.05}Li_{0.1}Fe_{0.05}O)_2P_2O_7\pm\delta$.

EXAMPLE 18

Preparation of $(V_{0.81}Sb_{0.09}Ce_{0.1}O)_2P_2O_7\pm\delta$

The procedure described in Example 14 were used. The cation sources were as shown in Table I and were used in the molar ratios shown. The formula of the catalyst produced was $(V_{0.81}Sb_{0.09}Ce_{0.1}O)_2P_2O_7\pm\delta$.

EXAMPLE 19

Preparation of $(V_{0.9}Sb_{0.05}Ni_{0.05}O)_2P_2O_7\pm\delta$

The procedure described in Example 7 was used. The cation sources were as shown in Table I and were used in the molar ratios shown. The formula of the catalyst produced was $(V_{0.09}Sb_{0.05}Ni_{0.05}O)_2P_2O_7\pm\delta$.

EXAMPLE 20

Preparation of $(V_{0.9}Sb_{0.05}Cr_{0.05}O)_2P_2O_7$

The procedure described in Example 2 was used. The cation sources were as shown in Table I and were used in the molar ratios shown. The formula of the catalyst produced was $(V_{0.9}Sb_{0.05}Cr_{0.05}O)_2P_2O_7\pm\delta$.

EXAMPLE 21

Preparation of $(V_{0.9}Bi_{0.05}Sb_{0.05}O)_2P_2O_7$

A procedure similar to that described in Example 6 was used. A 3 liter round bottom flask was equipped with an addition funnel, mechanical stirrer and a reflux condenser. For the duration of the reflux, nitrogen gas was used to purge the apparatus. In an inert atmosphere drybox containing nitrogen gas, 89.89 g of vanadium pentoxide (Aldrich Chemicals, Milwaukee, Wis.) was added to the round bottom flask. The vanadium pentoxide was then air micronized. 17.32 g of $BiCl_3$ (Johnson, Matthey—Alfa Chemicals, Ward Hill, Mass.) and 16.43 g of $SbCl_5$ (JM, Alfa Chemicals) were then added. To this mixture, 1034 ml of isobutyl alcohol (anhydrous, Aldrich Chemicals) and 95 ml of benzyl alcohol (anhydrous, Aldrich Chemicals) were added. The round bottom flask was then stoppered and brought outside of the drybox. Anhydrous phosphoric acid was prepared in the inert atmosphere dry box by mixing 88.8 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brought outside of the drybox, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids are then filtered in a buchner funnel and dried in flowing nitrogen at 125° C. for a period of 16 hours to yield the catalyst precursor.

Following this procedure, the precursor was directly calcined and activated in a small, 4 cm fluidized bed reactor, to generate the active catalyst phase by subjecting the precursor to the thermal conditions detailed below:

25°–390° C. in air

390° C. 1 hr in air

390° C. 1 hour in 1.5% butane/air

390°–460° C. 20 minutes in 1.5% butane/air

460°–460° C. 18 hours in 1.5% butane/air

460°–420° C. in 1.5% butane air

420°–360° C. in 1.5% butane/air

360° C.–25° C. in $N_2$

Prior to the activation, fine particles were sieved out by using a 400 mesh screen.

EXAMPLE 22

Preparation of $(V_{0.9}Bi_{0.05}Sb_{0.05}O)_2P_2O_7\pm\delta$

The procedure described in Example 21 was used. The cation sources were as shown in Table I and were used in the molar ratios shown. The formula of the catalyst produced was $(V_{0.9}Bi_{0.05}Sb0.05O)_2P_2O_7\pm\delta$.

EXAMPLES 23–28

Preparation of $(V_{1-x-y}A_xB_yO)_2P_2O_7\pm\delta$

The procedure described in Example 7 was used. The cation sources were as shown in Table I and were used in the molar ratios shown. The formulas of the catalysts produced were $(V_{0.9}Bi_{0.05}Sb_{0.05}O)_2P_2O_7\pm\delta$, $(V_{0.9}Bi_{0.05}Sb_{0.05}O)_2P_2O_7\pm\delta$, $(V_{0.9}Sb_{0.05}Sn_{0.05}O)_2P_2O_7$, $(V_{0.9}Sb_{0.05}Ga_{0.05}O)_2P_2O_7$, $(V_{0.9}Sb_{0.05}Co_{0.05}O)_2P_2O_7\pm\delta$, and $(V_{0.8}Sb_{0.1}Co_{0.1}O)_2P_2O_7\pm\delta$.

TABLE I

| Example No. | Cation Substituents B, A | Mole Ratio of V:B:A | Sources of cation substituent B, A |
|---|---|---|---|
| 2 | Fe, Sb | 0.98:0.01:0.01 | $FeCl_3$, $Sb(OC_4H_9)_3$ |
| 3 | Fe, Sb | 0.8:0.1:0.1 | $FeCl_3$, $Sb(OC_4H_9)_3$ |
| 4 | Fe, Sb | 0.9:0.075:0.025 | $FeCl_3$, $Sb(OC_4H_9)_3$ |
| 5 | Fe, Sb | 0.9:0.025:0.075 | $FeCl_3$, $Sb(OC_4H_9)_3$ |
| 6 | Fe, Sb | 0.9:0.05:0.05 | $FeCl_3$, $SbCl_5$ |
| 7 | Fe, Sb | 0.9:0.05:0.05 | $FeCl_3$, $Sb(OC_4H_9)_3$ |
| 8 | Fe, Sb | 0.9:0.05:0.05 | Iron(III)pentanedionate, $Sb(OC_4H_9)$ |
| 9 | Fe, Sb | 0.8:0.1:0.1 | Iron(III)pentanedionate, $Sb(OC_4H_9)$ |
| 10 | Fe, Sb | 0.8:0.05:0.15 | $FeCl_3$, $Sb(OC_4H_9)_3$ |
| 11 | Cu, Sb | 0.9:0.05:0.05 | Copper oxide, $Sb(OC_4H_9)_3$ |
| 12 | Cu, Sb | 0.9:0.05:0.05 | Cu(II)2,4 pentanedionate dehydrate, $Sb(OC_4H_9)_3$ |
| 13 | Mn, Sb | 0.9:0.05:0.05 | Manganese(II) acetylacetonate, $Sb(OC_4H_9)_3$ |
| 14 | Mn, Sb | 0.8:0.1:0.1 | Manganese(II) acetylacetonate, $Sb(OC_4H_9)_3$ |
| 15 | Al, Sb | 0.9:0.05:0.05 | Aluminum isopropoxide, $Sb(OC_4H_9)_3$ |
| 16 | Al, Sb | 0.6:0.2:0.2 | Aluminum isopropoxide, $Sb(OC_4H_9)_3$ |
| 17 | Li, Fe, Sb | 0.8:0.1:0.05:0.05 | Lithium benzoate, FeCl3, $Sb(OC_4H_9)_3$ |
| 18 | Ce, Sb | 0.81:0.1:0.09 | $CeO_2$, $Sb(OC_4H_9)_3$ |
| 19 | Ni, Sb | 0.9:0.05:0.05:1 | Nickel(II)pentanedionate, $Sb(OC_4H_9)_3$ |
| 20 | Cr, Sb | 0.9:0.05:0.05 | Chromium(III) acetate hydroxide, $Sb(OC_4H_9)_3$ |
| 21 | Bi, Sb | 0.9:0.05:0.05 | $BiCl_3$, $SbCl_5$ |
| 22 | Bi, Sb | 0.9:0.05:0.05 | $BiCl_3$, $Sb(OC_4H_9)_3$ |
| 23 | Bi, Sb | 0.9:0.05:0.05 | $BiCl_3$, $SbCl_5$ |
| 24 | Bi, Sb | 0.9:0.05:0.05 | Bismuth 2-ethylhexanoate, $Sb(OC_4H_9)_3$ |
| 25 | Sn, Sb | 0.9:0.05:0.05 | Tin(II)ethoxide, $Sb(OC_4H_9)_3$ |
| 26 | Ga, Sb | 0.9:0.05:0.05 | $GaCl_3$, $Sb(OC_4H_9)_3$ |
| 27 | Co, Sb | 0.9:0.05:0.05 | Co(II)2,4 pentanedionate, $Sb(OC_4H_9)_3$ |
| 28 | Co, Sb | 0.8:0.1:0.1 | Co(II)2,4 pentanedionate, $Sb(OC_4H_9)_3$ |

COMPARATIVE EXAMPLE A

Preparation of $(VO)_2P_2O_7$

The procedure of Example 7 (correcting for the stoichiometry by replacing Fe and Sb with an equimolar amount of vanadium to make a VPO catalyst) was followed except that no antimony butoxide nor iron chloride were used. The formula of the catalyst produced was $(VO)_2P_2O_7$.

COMPARATIVE EXAMPLE B

Preparation of $(V_{0.9}Cr_{0.1}O)_2P_2O_7$

The procedure of Example 2 was followed except that Chromium(III) acetate hydroxide alone was used instead of antimony butoxide and iron chloride. The formula of the catalyst produced was $(V_{0.9}Cr_{0.1}O)_2P_2O_7$.

COMPARATIVE EXAMPLE C

Preparation of $(V_{0.9}Fe_{0.05}Cr_{0.0}O)_2P_2O_7$

The procedure of Example 14 was followed except that Chromium(III) acetate hydroxide was used instead of manganese acetyl acetoate. The formula of the catalyst produced was $(V_{0.9}Fe_{0.05}Cr_{0.05}O)_2P_2O_7$.

EXAMPLE 29

Conversion/Selectivity data in pulsed micro-reactor

The catalysts in accordance with this invention from Example 1, Comparative Example A, Comparative Example B and Comparative Example C prepared above were utilized in the pulsed microreactor described below to catalyze the conversion of butane to maleic anhydride.

Figure 1:
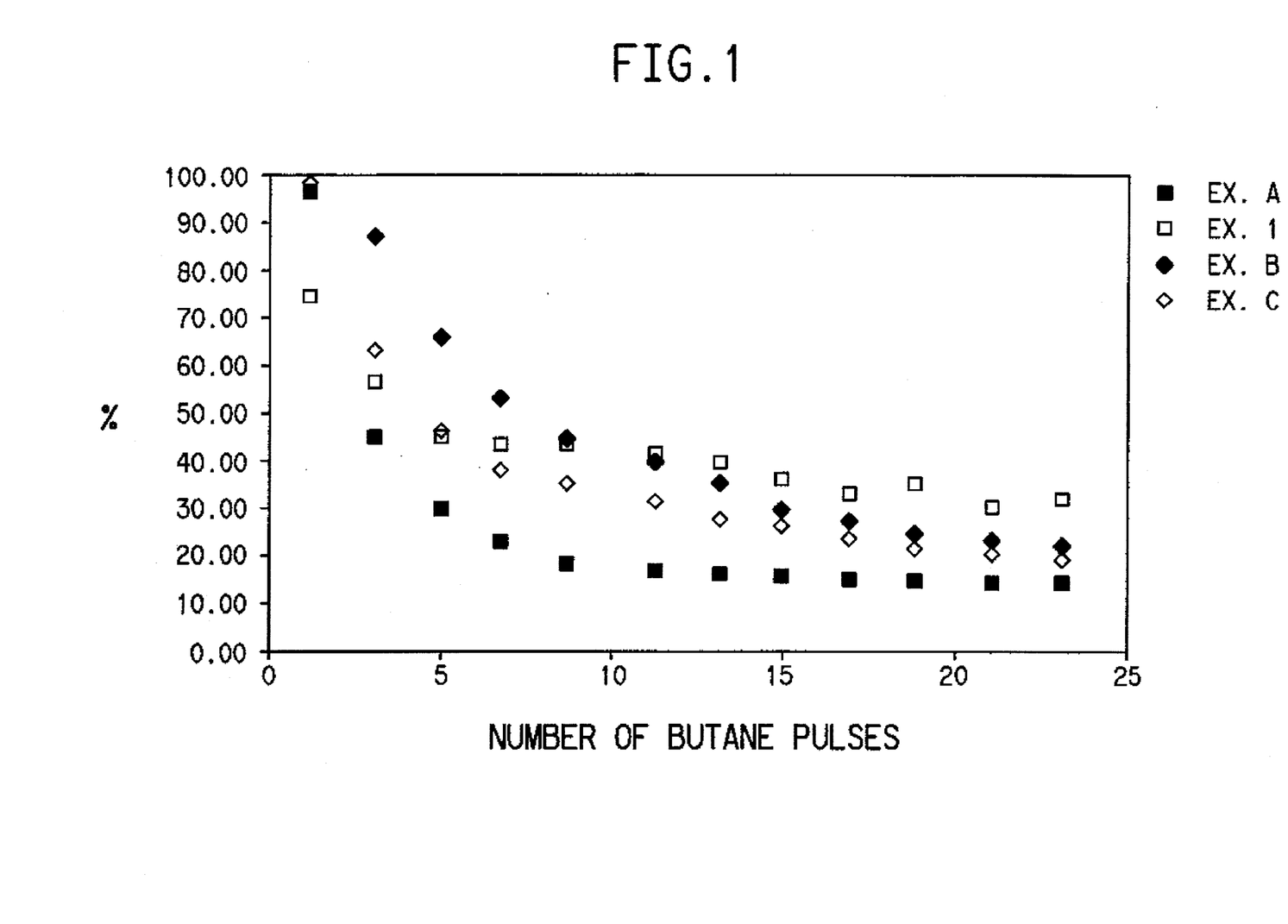
FIG. 1 is a chart of the percent conversion of n-butane to maleic anhydride versus the number of n-butane pulses utilized in a pulsed micro-reactor generated as described in Example 29. The white box represents a catalyst of the present invention, $(V_{0.9}Sb_{0.05}Fe_{0.05}O)_2P_2O_7$ prepared as described in Example 1. The black box represents $(VO)_2P_2O_7$ prepared as in Comparative Example A. The black diamond represents $(V_{0.9}Cr_{0.1}O_2)P_2O_7$ prepared as in Comparative Example B. The white diamond represents $(V_{0.9}Cr_{0.05}Fe_{0.05}O)_2P_2O_7$ prepared as in Comparative Example C.
Figure 2:
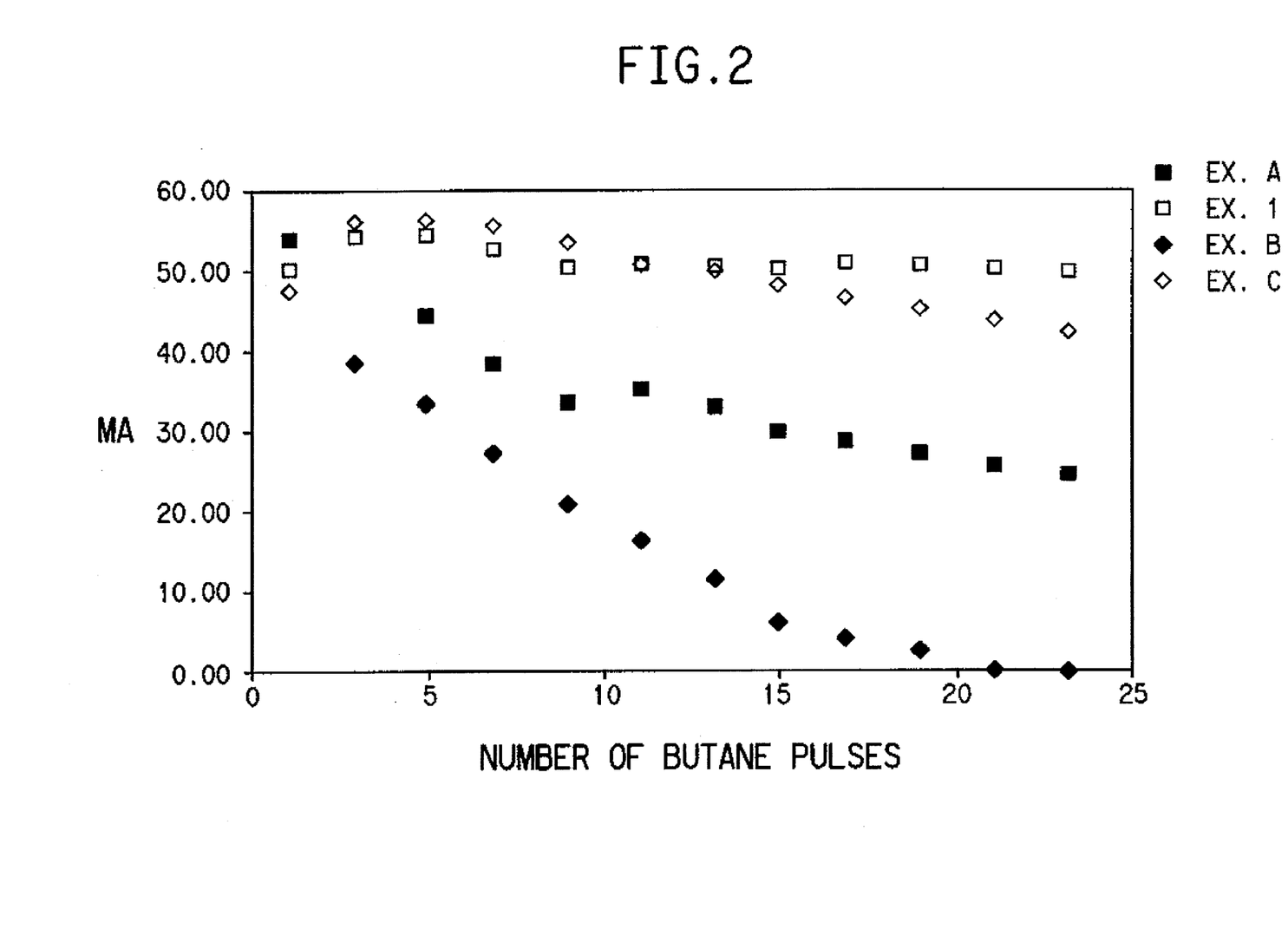
FIG. 2 is a chart of the selectivity to maleic anhydride versus the number of n-butane pulses utilized in a pulsed micro-reactor generated as described in Example 29. The white and black boxes and diamonds represent the same compounds as described above for FIG. 1.

Pulse reactor evaluation of the catalysts was carried out by injecting 0.05 ml pulses of butane by means of a gas sampling valve contained in an oven at 170° C. into a stream of helium flowing at 10 ml/min that passed over 0.5 grams of catalyst in a reactor made from ⅛ (3.2 mm) tubing and heated in a tube furnace to 380° C. The effluent of the reactor passed through a thermal conductivity detector and then through a sample loop. When the pulse was in the sample loop, as determined by the thermal conductivity detector, it was injected into a gas chromatograph for analysis of the reaction products. Butane pulses were passed over the catalyst every 10 min, with alternate pulses being analyzed. Butane conversions and selectivities to maleic anhydride with successive butane pulses are shown in FIGS. 1 and 2. These were calculated by the following formulas Butane conversion=butane in product/butane in feed.

Selectivity to maleic anhydride=moles maleic anhydride produced/moles butane reacted.

Pulsed microreactor evaluations of these catalysts showed differences between substituted vanadium phosphates and their parent compounds as shown in FIGS. 1 and 2. FIG. 1 shows that the catalyst was reduced with successive butane pulses. The catalyst of Example 1 maintained conversion levels relative to the Comparative Example A, Comparative Example B and Comparative Example C catalyst. FIG. 2 showed that as the catalyst was reduced with successive butane pulses, the catalyst of Example 1 maintained selectivity relative to the Comparative Example A, Comparative Example B and Comparative Example C catalyst.

COMPARATIVE EXAMPLE D

Preparation of $(VO)_2P_2O_7$ with spray drying

Vanadium phosphate precursor, prepared as described in Example 7 (correcting for the stoichiometry by replacing Fe and Sb with an equimolar amount of vanadium to make a VPO catalyst), was repeated 14 times to yield 14 combined batches. This precursor was air micronized to a particle size less than 5 microns in diameter. 2000 g of this precursor was then slurried in 5% (wt % as $SiO_2$) of polysilicic acid (PSA). The 5% PSA was prepared by mixing 1014 g of sodium silicate with 5000 g of $H_2O$. The Na was then removed by combining with DOWEX HCR-W2 sulfonic acid resin (Dow Chemicals, Midland Mich.). The appropriate amount of PSA was used fresh. The time of contact of the slurry with the polysilicic acid was kept to less than about 30 minutes. The catalyst slurry was then spray dried to produce a final catalyst composition containing 10 wt % $SiO_2$.

This slurry was then poured through a cheesecloth, to filter out any very large clumps of catalyst, and then pumped into a commercially available spray dryer (Bowen Dryer, available from Bowen Engineering Corporation, Columbia, Md.). This spray dryer is a 4 ft diameter, 8 ft straight end electrically fired dryer. Typical spray drying conditions include a feed rate of 160 m./min, an inlet temperature of 376° C. to the dryer and outlet temperatures of 160°–170° C. The catalyst was then calcine activated in accordance with the procedure of Example 1.

EXAMPLE 30

Preparation of $(V_{0.9}Sb0.05Fe0.05O)_2P_2O_7 \pm \delta$ with spray drying

The procedure of Comparative Example D was followed except that the catalyst precursor used was prepared according to Example 7.

EXAMPLE 31

Preparation of $(V_{0.8}Sb0.1Fe0.1O)_2P_2O_7 \pm \delta$ with spray drying

The procedure of Example 7 was followed for the preparation of the precursor, correcting for the stoichiometry of iron and antimony. The resulting catalyst precursor was then treated in accordance with the procedure of Comparative Example D, except that g of micronized precursor was slurried with 700.4 g of 5% polysilicic acid prior to spray drying.

EXAMPLE 32

Preparation of $(V_{0.8}Sb_{0.05}Li_{0.1}Fe0.05O)_2P_2O_7 \pm \delta$ with spray drying The procedure of Example 31 was followed except for correcting for the stoichiometry of the catalyst precursor. Lithium benzoate was used for the source of lithium.

EXAMPLE 33

Preparation of $(V_{0.9}Sb_{0.05}Mn_{0.05}O)_2P_2O_7 \pm \delta$ with spray drying The procedure of Example 31 was followed except for correcting for the stoichiometry of the catalyst precursor. Manganese acetate and antimony butoxide were the sources of Mn and Sb.

EXAMPLE 34

Preparation of $(V_{0.6}Sb_{0.2}Al_{0.20}O)_2P_2O_7 \pm \delta$ with spray drying The procedure of Example 16 was followed to prepare two batches of the precursor which were subsequently micronized. They were spray dried and then calcined/activated in accordance with the procedure of Comparative Example 31.

EXAMPLE 35

Preparation of $(V_{0.9}Sb_{0.05}Cu_{0.05}O)_2P_2O_7 \pm \delta$ with spray drying The procedure of Example 11 was followed to prepare two batches of the precursors which were subsequently micronized. The precursor was spray dried and then calcined/activated in accordance with the procedure of Comparative Example 31.

EXAMPLE 36

Preparation of $(V_{0.9}Fe_{0.1})_2P_{1.8}Bi_{0.2}O_7 \pm \delta$ with spray drying Two batches of the commercial precursor was prepared using the 3 liter reflux apparatus described in Example 7. The procedure used was similar to Example 7, except for the reagents. 89.89 g of vanadium pentoxide, 17.82 g of iron trichloride (anhydrous), 77.93 g of bismuth 2-ethylhexanoate were used. The amount of phosporic acid and phosphorus pentoxide used were 29.88 and 29.88 g, respectively.

Two batches of this precursor was prepared, spray dried and calcined/activated according to the procedure of Example 31.

EXAMPLE 37

Conversion/Selectivity data in fixed bed-reactor

A fixed bed micro-reactor was used to evaluate the catalysts from Comparative Example D and Examples 30–36, inclusive. The microreactor consisted of a 40.64 cm by 0.64 cm stainless steel tube enclosed by an aluminum sheath (3.12 cm thick, to assist in minimizing thermal gradients) which itself was enclosed in a tube furnace. The reactor was mounted vertically with the direction of the of gas flow from top to bottom. Pressure gauges were mounted near both the entrance and exit of the reactor to monitor pressure changes. A bypass valve installed near the reactor entrance allowed the entering gas stream to pass through either the reactor or to bypass the reactor and pass directly to the sampling valve system, allowing analysis of the reactor feed gases prior to reaction. Also, a T connection at the top of the reactor allowed a thermocouple to be mounted such that it monitored the temperature at the entrance to the packed catalyst bed. Commercially available mass flowmeters (Tylan Model FC-260) of ranges 0–100 and 0–10 cc/minute, respectively, fed the reactor. The heated exit gas stream (200° C.) passed through a heated sampling valve allowing the selection of a gas sample (250 μl ) of the stream for analysis by gas-liquid chromatography (GLC), using a commercially available instrument (Gow-Mac Series 740P FID GLC). The GLC was used to analyze for butane and for products to maleic anhydride, acetic acid and acrylic acid.

The pseudo-first order rate constant, k, given for the disappearance of butane in the Table was obtained by fitting the reactor data to a classical first order rate expression:

d[butane]/dt=−k[butane]

d(xo−x)/dt=−k(xo−x)

where xo=initial conc. of butane x=portion of butane reacted

Integrating this expression gave the concentration of butane exiting the reactor as a function of contact time, t, in the reactor:

$$[\text{exit butane}] = xo - x = xo^{-kt}$$

In addition to describing the reaction rate of butane with a catalyst, the rate constant k included several other factors including the dependence of the reaction rate on oxygen concentration (which remained relatively constant under our conditions) and the concentration of catalyst active sites (also assumed constant).

Rate constants and selectivity at 40% conversion is shown in Table 2.

TABLE 2

Spray Dried Catalysts

| Example | Mole Ratio of V:A:B:P | k (sec)$^{-1}$ | Selectivity at 40% conversion |
|---|---|---|---|
| D | 1:0:0:~1 | 1.15 | 49 |
| 30 | 0.9:0.05:0.05:~1 | 1.18 | 74 |
| 31 | 0.8:0.1:0.1:~1 | 1.25 | 65 |
| 32 | 0.0.05:8:0.1:0.05:~1 | 0.53 | 46 |
| 33 | 0.9:0.05:0.05:~1 | 1.00 | 52 |
| 34 | 0.6:0.2:0.2:~1 | 0.66 | 19 |
| 35 | 0.9:0.05:0.05:~1 | 2.54 | 67 |
| 36 | 1.8:0.2:0.2:~1.8 | 0.63 | 15 |

EXAMPLE 38

X-ray diffraction

X-ray data Were obtained at room temperature on the catalysts prepared in accordance with Examples 1, 4, 21, 20, 11, 25, 26 and Comparative Example A using a conventional commercially available diffractometer (Philips XRD 3600 powder diffractometer with CuKalpha radiation), using 0.02 C 2θ steps and 0.5 seconds count time per step. Cell parameters were refined with the aid of a least squared fitting program which corrected for random errors, as well as the systematic error effects of the diffractometer. All d-spacings were calculated on the basis of the CuKα1 line (1.5405 Å) (0.15405 nm) and included the systematic error corrections. The listed 2-theta values are uncorrected for the systematic errors. The x-ray diffraction data analyisis showed the activated catalysts in accordance with this invention closely resembled single phase $\beta(VO)_2P_2O_7$, with substantially no trace of separate promoter phases.

The results are shown in Table 3.

TABLE 3

| Example No. | X-ray Diffraction Data* | | | |
|---|---|---|---|---|
| | a (Å) | b (Å) | c (Å) | V (Å$^3$) |
| A | 9.59(1) | 7.76(2) | 16.59(1) | |
| 1 | 9.68 | 7.76 | 16.63 | 1249 |
| 4 | 9.57 | 7.84 | 16.6 | 1245 |
| 21 | 9.57 | 7.77 | 16.55 | 1231 |
| 20 | 9.62 | 7.74 | 16.6 | 1236 |
| 11 | 9.59 | 7.82 | 16.55 | 1241 |
| 25 | 9.58 | 7.80 | 16.57 | 1238 |
| 26 | 9.6 | 7.76 | 16.56 | 1234 |

*1Å = 0.1 nm

COMPARATIVE EXAMPLE E

Preparation of $(VO)_2P_2O_7/SiO_2$ and Conditioning in Circulating Solids Reactor The procedure of Comparative Example D was followed, except that the catalyst was further conditioned in a circulating solids reactor as described in U.S. Pat. No. 4,668,802, wherein the amount of oxygen in the feed gas to the catalyst was limited to less than the stoichiometric amount required for the total amount of n-butane converted in the process. The reduced catalyst resulting from the oxidation was separated from the gaseous product stream; and was reoxidized, optionally in a separate reaction zone, before being contacted with n-butane in a pulsed micro reactor as described in Example 29.

Figure 3:
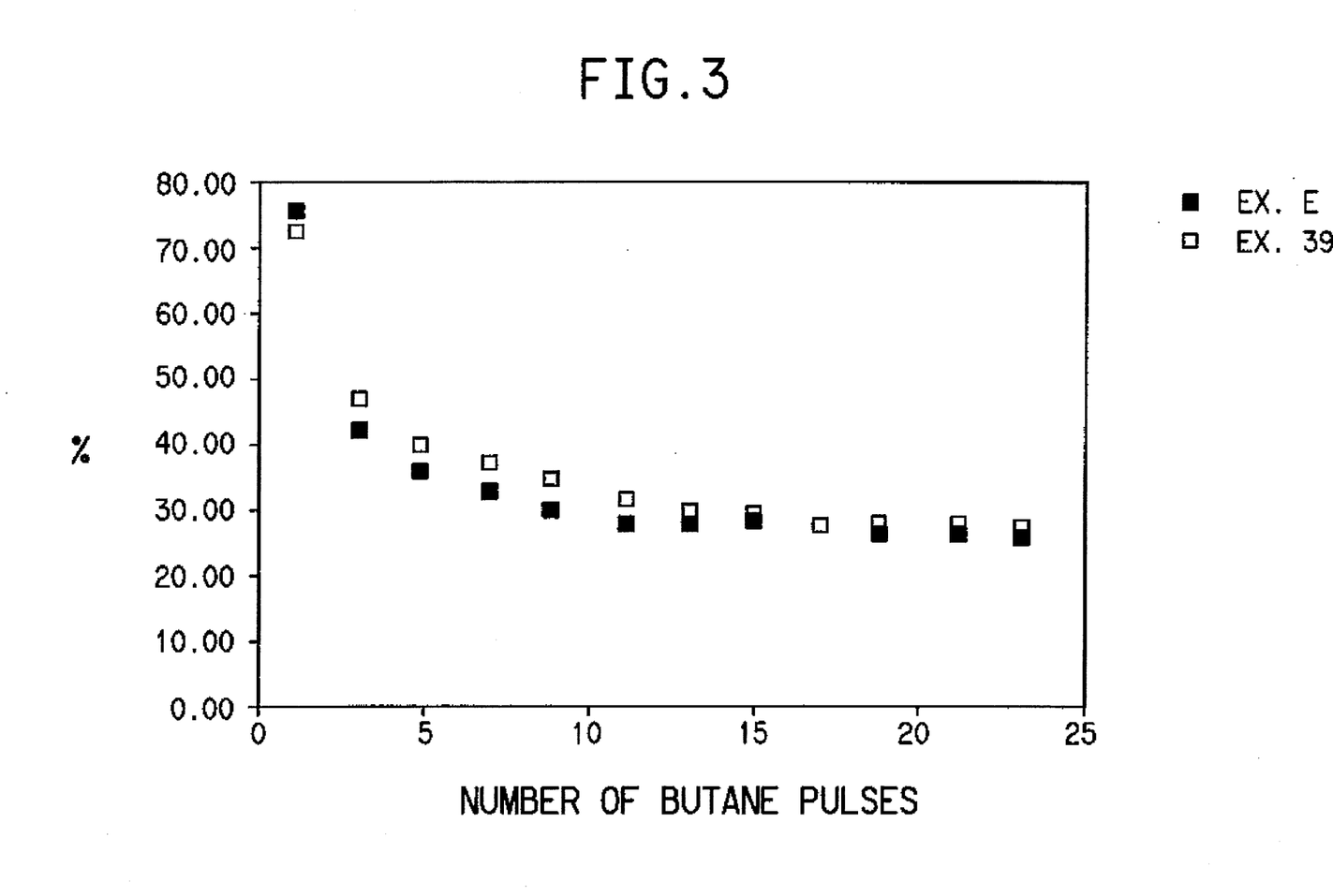
FIG. 3 is a chart of the percent conversion of n-butane to maleic anhydride versus the number of n-butane pulses utilized in a pulsed micro-reactor for spray dried catalyst with 10 wt % silica generated as described in Example 39. The white box represents a catalyst of the present invention, $(V_{0.9}Sb_{0.05}Fe_{0.05}O)_2P_2O_7/SiO_2$ prepared as in Example 39. The black box represents $(VO)_2P_2O_7/SiO_2$ prepared as in Comparative Example E.
Figure 4:
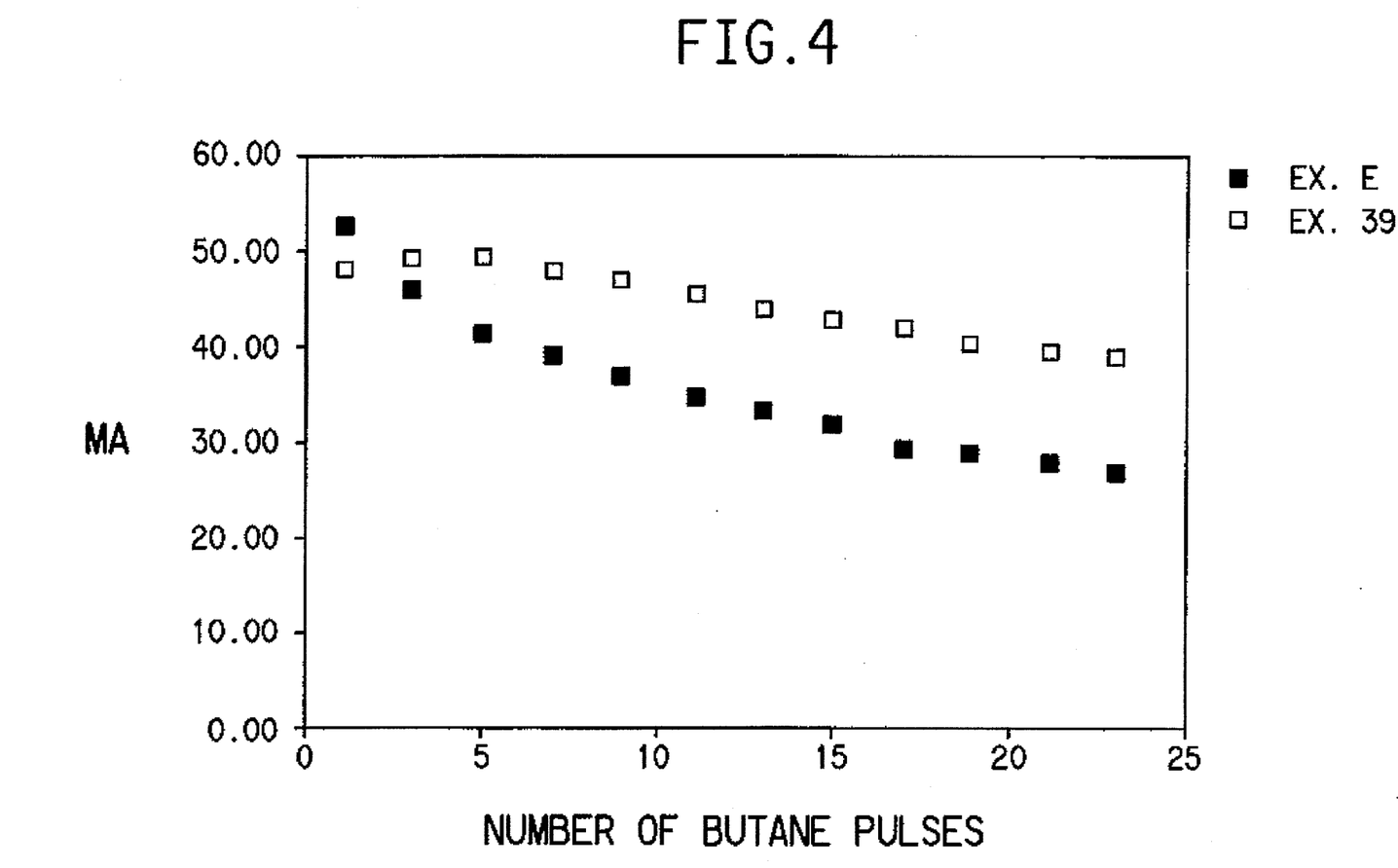
FIG. 4 is a chart of the selectivity to maleic anhydride versus the number of n-butane pulses utilized in a pulsed micro-reactor for spray dried catalyst with 10 wt % silica generated as described in Example 39. The white and black boxes represent the same compounds as described above for FIG. 3.

Conversion and selectivity versus the number of butane pulses is shown in FIGS. 3 and 4, respectively.

EXAMPLE 39

Preparation of $(V_{0.9}Fe_{0.05}Sb_{0.05}O)_2P_2O_7\pm\delta/SiO_2$ and Conditioning in Circulating Solids Reactor The procedure of Example 30 was followed, except that the catalyst was further conditioned in a circulating solids reactor in accordance with Comparative Example D.

Conversion and selectivity versus the number of butane pulses is shown in FIGS. 3 and 4, respectively. It is seen from FIG. 4 that the catalyst in accordance with the invention (Example 39) maintained selectivity relative to the Comparative Example D with successive butane pulses.

What is claimed is:

1. An improved vanadium phosphorus oxygen catalyst for the oxidation of alkane hydrocarbons wherein the improvement comprises the presence of two different promoters A and B in the catalyst, said catalyst comprising a crystalline oxide of formula I through IV $(V_{1-x-y}A_xB_yO)_2P_2O_7\pm\delta$     I $(V_{1-x}A_xO)_2P_{2-y}B_yO_7\pm\delta$     II $(V_{1-y}B_yO)_2P_{2-x}A_xO_7\pm\delta$     III $(VO)_2P_{2-x-y}A_xB_yO_7\pm\delta$     IV wherein A is a cation of Sb and B is a cation of Fe or A is a cation of Bi and B is a cation of Mo;

$\delta$ is 0 to less than 0.5; and x and y are as follows:

in formula I: $0.7 \geq x > 0$ for each A, $0.7 \geq y > 0$ for each B, and $0.7 \geq (x+y) > 0$;

in formula II: $0.7 \geq x > 0$ for each A, and $1.0 \geq y > 0$ for each B;

in formula III: $1.0 \geq x > 0$ for each A, and $0.7 > y > 0$ for each B; and in formula IV: $1.0 > x > 0$ for each A, $1.0 > y > 0$ for each B, and $1 \geq (x+y) > 0$.

2. The catalyst of claim 1 in the form of a solid solution.

3. The catalyst of claim 1 wherein, in the catalyst preparation, the promoters A and B are introduced into the reaction medium as inorganic salts.

4. The catalyst of claim 3 wherein, in the catalyst preparation, the promoters A and B are each independently introduced into the reaction medium as a salt selected from the group consisting of an acetate, alkoxide, anhydrous halide, and acetylacetonate.

5. An improved process for the oxidation of n-butane to maleic anhydride using a vanadium phosphorus oxygen catalyst wherein the improvement comprises using a catalyst comprising a crystalline oxide of formula I through IV $(V_{1-x-y}A_xB_yO)_2P_2O_7\pm\delta$     I $(V_{1-x}A_xO)_2P_{2-y}B_yO_7\pm\delta$     II $(V_{1-y}B_yO)_2P_{2-x}A_xO_7\pm\delta$     III $(VO)_2P_{2-x-y}A_xB_yO_7\pm\delta$     IV wherein A is a cation of Sb and B is a cation of Fe or A is a cation of Bi and B is a cation of Mo:

$\delta$ is 0 to less than 0.5; and x and y are as follows:

in formula I: $0.7 \geq x > 0$ for each A, $0.7 \geq y > 0$ for each B, and $0.7 \geq (x+y) > 0$;

in formula II: $0.7 \geq x > 0$ for each A, and $1.0 \geq y > 0$ for each B;

in formula III: $1.0 \geq x > 0$ for each A, and $0.7 \geq y > 0$ for each B; and in formula IV: $1.0 > x > 0$ for each A, $1.0 > y > 0$ for each B, and $1 \geq (x+y) > 0$.

6. The process of claim 5 wherein the catalyst is the only source of oxygen.

7. The process of claim 5 wherein the oxidation is carried out in a recirculating solids reactor.

* * * * *